US009266849B2

(12) United States Patent
Gu et al.

(10) Patent No.: US 9,266,849 B2
(45) Date of Patent: Feb. 23, 2016

(54) PROCESS FOR RECOVERING DIVINYLARENE DIOXIDES

(71) Applicant: Blue Cube IP LLC, Midland, MI (US)

(72) Inventors: Leming Gu, Lake Jackson, TX (US); William W. Fan, Lake Jackson, TX (US); Bruce D. Hook, Lake Jackson, TX (US); David Jean, Friendswood, TX (US); Dennis W. Jewell, Angleton, TX (US)

(73) Assignee: Blue Cube IP LLC, Midland, MI (US)

( * ) Notice: Subject to any disclaimer, the term of this patent is extended or adjusted under 35 U.S.C. 154(b) by 0 days.

(21) Appl. No.: 14/356,989

(22) PCT Filed: Nov. 27, 2012

(86) PCT No.: PCT/US2012/066572
§ 371 (c)(1),
(2) Date: May 8, 2014

(87) PCT Pub. No.: WO2013/085743
PCT Pub. Date: Jun. 13, 2013

(65) Prior Publication Data
US 2015/0232437 A1    Aug. 20, 2015

Related U.S. Application Data

(60) Provisional application No. 61/567,827, filed on Dec. 7, 2011.

(51) Int. Cl.
*C07D 301/32*    (2006.01)
(52) U.S. Cl.
CPC .................... *C07D 301/32* (2013.01)

(58) Field of Classification Search
CPC ..................................... C07D 301/32
USPC ........................................... 549/541
See application file for complete search history.

(56) References Cited

U.S. PATENT DOCUMENTS 2,924,580 A    2/1960    Phillips et al.
2,977,374 A    3/1961    Phillips et al.
(Continued)

FOREIGN PATENT DOCUMENTS

EP    0878471 A1    11/1998
EP    1841753 B1    8/2009
(Continued)

OTHER PUBLICATIONS

M. Worzakowska, Influence of Cure Schedule on the Viscoelastic Properties and Thermal Degradation of Crosslinked Mono-and Diepoxides Obtained During the Reaction of Hydrogen Peroxide and Divinylbenzene, J. Appl. Poly. Sci. (2007), pp. 462-469, vol. 103.
Masami Inoue, Effect of Anions on the Epoxidation of Styrenes with H2O2 in the Presence of Ammonium Heptamolybdate(VI)-Dioctyltin Oxide Catalysts, Bull. Chem. Soc. Jpn, pp. 3442-3444, (1991), vol. 64, No. 11.

*Primary Examiner* — T. Victor Oh

(57) ABSTRACT

A process for recovering a divinylarene dioxide from a crude feed stream comprising the steps of: (a) providing an effluent reaction stream containing at least one divinylarene dioxide product and other compounds; and (b) separating/recovering the divinylarene dioxide product from the other compounds of the reaction effluent from step (a); wherein the percent recovery of the divinylarene dioxide product recovered comprises greater than about 85 percent; and wherein the percent purity of the divinylarene dioxide product recovered comprises greater than about 85 percent.

11 Claims, 5 Drawing Sheets

(56) References Cited

U.S. PATENT DOCUMENTS

| | | | |
|---|---|---|---|
| 2,982,752 A | 5/1961 | Phillips et al. | |
| 4,304,639 A | 12/1981 | Hardy et al. | |
| 8,674,122 B2 | 3/2014 | Ripplinger et al. | |
| 8,716,502 B2 | 5/2014 | Gu et al. | |
| 2012/0253055 A1* | 10/2012 | Ripplinger et al. | 549/529 |

FOREIGN PATENT DOCUMENTS

| | | | |
|---|---|---|---|
| WO | 2010/101144 A1 | | 9/2010 |
| WO | WO2011084687 | * | 7/2011 |
| WO | WO2011/116180 | * | 9/2011 |
| WO | WO2011116177 | * | 9/2011 |

* cited by examiner

PROCESS FOR RECOVERING DIVINYLARENE DIOXIDES

BACKGROUND OF THE INVENTION

1. Field of the Invention

The present invention is related to a process for recovering divinylarene dioxides, particularly divinylarene dioxides derived from divinylbenzene. More specifically, the present invention relates to a process for recovering a divinylarene dioxide from a crude feed stream, for example, a stream resulting from an epoxidation process for preparing a divinylarene dioxide.

2. Description of Background and Related Art

There are various known processes for preparing a divinylarene dioxide such as a divinylbenzene dioxide (DVBDO). For example, U.S. Pat. No. 2,977,374 ("the '374 patent"), incorporated herein by reference, discloses epoxidizing divinylbenzene (DVB) using peracetic acid in ethyl acetate and reports a DVBDO yield of 49 percent (%). The '374 patent teaches recovery of an epoxidized product by continuous distillation in two passes; removal of lights such as solvent and byproduct acetic acid in a first pass; and recovery of overhead product in a second pass. An example is provided in the '374 patent for DVBDO that describes two "stripper" passes to remove lights and a "flash distillation" to recover the product overhead. The '374 patent discloses obtaining a low DVBDO purity (59 weight percent) and a low yield as reported in the example; thus, the process described in the '374 patent results in neither a high distillation recovery nor a high purity product.

M. Worzakowska, *J. Appl. Poly. Sci.* (2007) vol. 103, pp. 462-469, incorporated herein by reference, discloses epoxidizing DVB using acetonitrile-hydrogen peroxide in the presence of a magnesium oxide catalyst and greater than a 4-fold molar excess of hydrogen peroxide to olefin. The above Worzakowska article does not describe the use of distillation, and only discloses that the epoxides are "separated from the solvents and byproduct". However, given the recovered product purity is only about 45%, while starting with a 65% divinylbenzene raw material purity, this process has both a low product purity, and a low distillation recovery.

U.S. Pat. No. 4,304,639 ("the '639 patent") discloses a process for the purification of olefin oxides and describes a continuous distillation scheme using a small amount of water and a side draw with decant. The process described in the '639 patent is directed to the preparation of propylene oxide (PO). DVBDO is listed as one of a long list of potential epoxides that can be prepared using the process described in the '639 patent. However, the description in the '639 patent is insufficient to enable the skilled artisan to determine how the process might result in high distillation recovery of DVBDO or high DVBDO purity.

EP0878471A1 ("EP471") discloses reactive radiation-initiated or thermally-initiated cationically-curable epoxide monomers and compositions made from those monomers; and describes the synthesis of DVBDO using Oxone. The workup described in EP471 includes removal of solvents "in vacuo at 35° C.", with no further purification. EP471 teaches that 5 mL of DVB (4.58 g) (theoretical product approximately 5.7 g) yields 4.92 g of product which is an overall yield of 86%. The description in EP471 is insufficient to enable the skilled artisan to determine the distillation recovery or the purity of the recovered product. The product, as described in EP471, is not separated from any heavies present, i.e., the process of EP471 does not provide a distillation or separation step in its disclosed process to achieve a high purity of divinylarene dioxide.

EP1841753B1 ("EP753") discloses a process for the epoxidation of an olefin with an improved energy balance. The disclosure in EP753 is focused on preparing PO from propylene, but generally claims the epoxidation of an "olefin". EP753 teaches DVB as an olefin. In addition, EP753 teaches using a dividing wall column, distillation, and "distillative separations processes" in the recovery description (the focus of EP753 is on recovery of unreacted olefin, solvent, and product). The description in EP753 is insufficient to enable the skilled artisan to determine or define a high distillation recovery or high DVBDO purity process.

WO 2010/101144A1 discloses epoxy resin composition and describes processes for epoxidation in general. One example describes synthesis of DVBDO using 30% peracetic acid in ethyl acetate. 300 g of DVB are used to produce 151.6 g of distilled DVBDO (only 41% overall yield). Separations are described as ethyl acetate removal by "reduced pressure distillation using an evaporator". High purity product (97.1% area %) is obtained by "purification using distillation" (10 torr, 150° C.). The description of the separations in WO 2010/101144A1 is insufficient to enable the skilled artisan to determine distillation recovery, however given the low overall yield of the product; the distillation recovery of the product is low.

Bull. Chem. Soc. Jpn, 64, 3442-3444 (1991) discloses the effect of anions on the epoxidation of styrenes with $H_2O_2$ in the presence of ammonium heptamolybdate(VI) dioctylin oxide catalysts. The product recovered by the above process is only described as being "separated" and the highest DVBDO overall yield described is 9.9%.

U.S. Pat. No. 2,982,752 discloses a composition comprising a polyepoxide and divinylbenzene dioxide and describes epoxidation of divinylbenzene (DVB) using peracetic acid solution in acetone or ethyl acetate. The patent further discloses "isolation of epoxide product by fractional distillation".

U.S. Pat. No. 2,924,580 discloses a divinylbenzene dioxide composition; however, there is no mention of how DVBDO is produced.

While the above processes for preparing a divinylarene dioxide are known, there is little attention paid to efficiently recovering the divinylarene dioxide product from a resultant crude feed stream containing divinylarene dioxide after the upstream reaction and processing for producing the divinylarene dioxide product is completed. None of the previously known processes described in the above references result in both a high distillation recovery and a high purity product. In addition, none of the above references teach a process including the recovery of monoepoxides at high recovery and/or high purity. In addition, none of the above references describe a process or conditions of a process to reduce the risk of runaway reaction. Furthermore, none of the above references describe a process that has been developed on an industrial scale for industrial use.

Previously, divinylarene dioxide process development by the industry focused on the production of vinyl arene oxide by oxidizing vinyl arenes to vinyl arene oxides. Known processes focused primarily with the chemistry of the reaction process and not the separations aspects of the process. Heretofore, a few known processes for the recovery of divinylarene oxides from a crude feed stream provided several disadvantages including (1) formation of heavies during the recovery process, (2) low recovery of product (e.g., less than (<) 85%) to achieve high product purity (e.g. greater than (>)

85%), (3) low purity of recovered monoepoxide by-product(s) (e.g., <85%), and/or (4) risk of a runaway reaction.

U.S. Patent Application Ser. No. 61/288,511 filed Dec. 21, 2009; and U.S. Patent Application Ser. No. 61/424,322 filed Dec. 17, 2010, disclose distillation of divinylarene epoxides. The above patent applications describe distillation of crude product to produce refined DVBDO at high purity, and conditions for temperature, pressure, and residence time. The above patent applications do not define a distillation recovery to achieve >85% purity of product; do not describe a distillation to achieve >85% purity and >85% recovery of monoepoxides; and do not describe the conditions required to reduce the risk of runaway reaction.

SUMMARY OF THE INVENTION

The present invention provides the industry with a process for the recovery of divinylarene dioxide product which may be practiced on an industrial scale; and provides high recovery of divinylarene dioxide product (>85%), at high purity (>85%), with minimal formation of undesirable contaminants or by-products. The present invention also provides a process with a reduced risk of runaway reaction. In addition, the present invention provides the industry with a process for the recovery of monoepoxide product(s) which may also be practiced on an industrial scale; and provides >85% recovery of monoepoxide product(s) at >85% purity.

One embodiment of the present invention is directed to a process for recovering a divinylarene dioxide product from a crude feed stream comprising the steps of: (a) providing a crude feed stream containing at least one divinylarene dioxide product and other compounds; and (b) separating/recovering the divinylarene dioxide product from the other compounds of the crude feed stream of step (a); wherein the percent recovery of the divinylarene dioxide product recovered comprises >85%; and wherein the percent purity of the divinylarene dioxide product recovered comprises >85%.

Another embodiment of the present invention provides a distillation process utilizing a combination of various apparatuses including for example one or more wiped film evaporators, one or more thin film evaporators, one or more short path evaporators, one or more falling film evaporators, one or more reboilers or one or more distillation columns, arranged in the proper sequence, and under the appropriate conditions to obtain a divinylarene dioxide product at >85% recovery and to obtain a pure divinylarene dioxide product having percent purity of >85%.

Using the process of the present invention the following advantages, for example, can be achieved: (1) no measurable formation of heavies during the recovery process; (2) product recovery of >85%, while achieving a product purity of >85%; (3) mono-epoxide(s) recovery of >85%, while achieving monoepoxide(s) purity of >85%; and (4) reduced risk of runaway reaction due to low residence time and minimized temperature of recovery process.

BRIEF DESCRIPTION OF THE DRAWINGS

For the purpose of illustrating the present invention, the following drawings show a form of the present invention which is presently preferred. However, it should be understood that the present invention is not limited to the precise arrangements and apparatuses shown in the drawings. In the accompanying drawings, like reference numerals are used to denote like parts throughout the several drawings.

DETAILED DESCRIPTION OF THE INVENTION

Definitions

Figure 1:
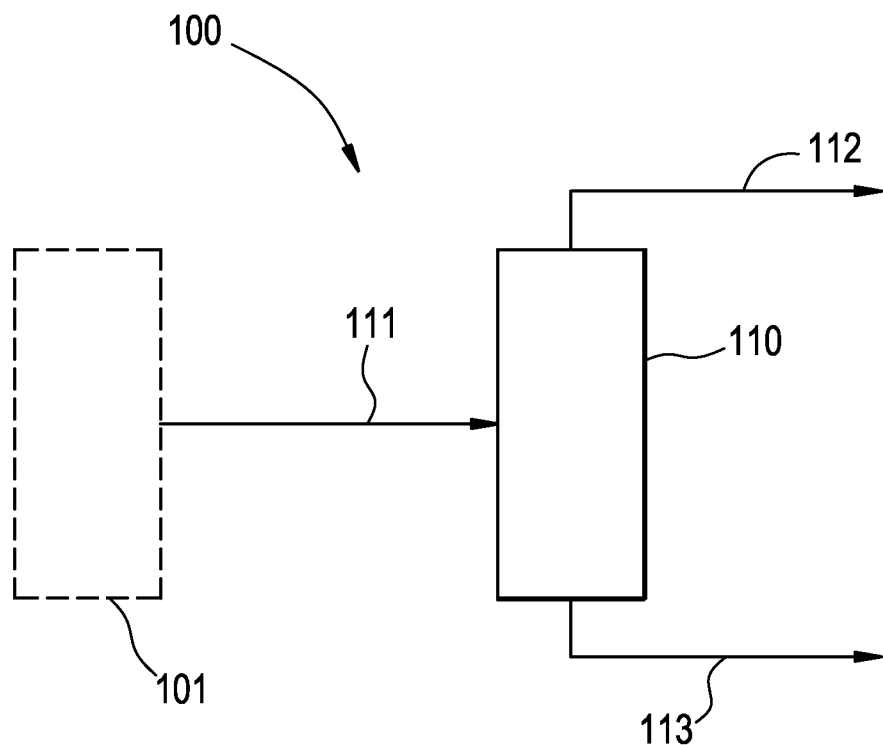
FIGS. 1-5 are flow diagrams showing various embodiments of the process of the present invention.

"Crude feed stream" herein means a mixture, effluent, or stream containing divinylarene dioxide product, and other compounds such as remaining unreacted reactants, water, basic compounds, lights, monoepoxide(s), heavies, solvent(s) and/or other additives such as inhibitors.

"Lights" herein means components having a volatility greater than the monoepoxides present in a given process stream as measured by vapor pressure for example wherein the vapor pressure of the lights is greater than the vapor pressure of the monoepoxides present in the stream. For example, the lights may include solvents such as methanol or toluene; water; naphthalene; nitriles such as acetonitrile; diethylarenes such as diethylbenzene, ethylvinylarenes such as ethylvinylbenzene; divinylarenes such as divinylbenzene; and mixtures thereof.

"Heavies" herein means components having a volatility less than the divinylarene dioxides present in a given process stream as measured by vapor pressure for example wherein the vapor pressure of the heavies is less than the vapor pressure of the divinylarene dioxides present in the stream. For example, the heavies may include divinylarene diols; oligomers of divinylarenes; and mixtures thereof.

"Monoepoxide(s) herein means ethylvinylarene oxides such as ethylvinylbenzene oxide (EVBO) and divinylarene monoxide such as divinylbenzene monoxide (DVBMO).

"No measurable formation of heavies" herein means that any heavies present in the crude feed stream is essentially equal to the heavies recovered in the outlet streams from the recovery process.

"Residence time" herein means the average amount of time that the process liquid spends in a system or apparatus. Residence time may be commonly calculated as the liquid hold-up volume of a system divided by the rate of liquid flow through the system.

"Low residence time" herein means time of less than 2 hours, at temperature greater than 60° C., for product containing streams.

"Runaway reaction" herein means an autocatalyzed, self-heating, exothermic reaction of the epoxide resulting in uncontrolled temperature and/or pressure increase.

"Reduced risk of runaway reaction" herein means operation at a temperature and residence time where runaway reaction has a lower probability of occurring.

"Percent purity (% purity)" herein means the mass concentration of a species in a process stream as measured by GC, and expressed as a percentage.

"Percent recovery (% recovery)" herein means the mass of a species obtained as a product divided by the mass of the species in the feed to the process expressed as a percentage.

"High purity" herein means greater than 85% purity of product such as of monoepoxide or of divinylarene dioxide.

"High recovery" herein means greater than 85% recovery of product.

"Wall temperature" herein means the temperature of the heat transfer surface at its interface with the process fluid. Wall temperature may also be commonly referred to as "skin temperature." Wall temperature is the actual temperature of the metal or alloy heat transfer surface in direct contact with the process fluid.

"Reynolds number" herein means a dimensionless number that represents the ratio of inertial forces to the viscous forces in fluid flow. Reynolds number may be typically calculated as velocity multiplied by density multiplied by characteristic length divided by the fluid viscosity. The velocity and characteristic length may be dependent upon the specific geometry of the apparatus. (See for example *Perry's Chemical Engineers' Handbook*, 6$^{th}$ ed., 1984.)

"Flux" herein means the mass flow rate of liquid divided by the cross sectional area of plane of flow orthogonal to the direction of flow. For example, for a film evaporator that cross sectional area is defined by the film thickness along the circumference of the evaporator.

The divinylarene dioxide-containing feed stream useful in the present invention process may come from any source including for example known processes for the preparation of divinylarene dioxide. For example, processes for preparing a divinylarene dioxide product are described in U.S. Patent Application Ser. No. 61/288,511 filed Dec. 21, 2009; and U.S. Patent Application Ser. No. 61/424,322 filed Dec. 17, 2010, both incorporated herein by reference. The source of a divinylarene dioxide-containing feed stream useful in the process of the present invention may be a crude mixture, effluent or stream resulting from any process for producing a divinylarene dioxide for example as described in the above references. Generally, the process for producing a divinylarene dioxide includes the epoxidation of divinylarene compounds in the presence of an oxidant and catalyst to obtain divinylarene dioxide compounds.

For example, one embodiment of a process for producing a divinylarene dioxide is shown in the following epoxidation reaction represented by the following reaction Scheme I:

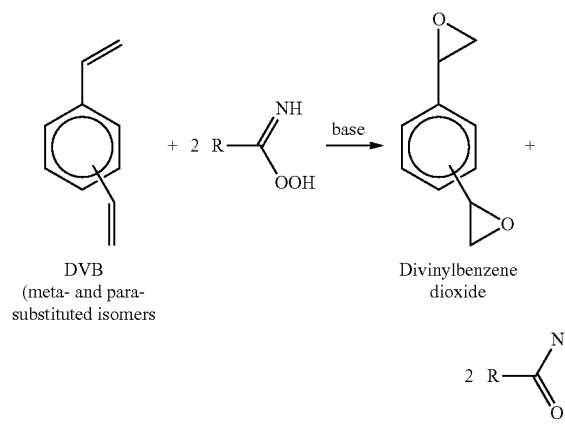

Scheme I above shows an epoxidation process wherein divinylbenzene (DVB) is epoxidized with a peroxycarboximidic acid.

The divinylarene dioxide-containing crude feed stream useful in the process of the present invention generally is the effluent from the epoxidation reaction described above and may contain, not only the divinylarene dioxide product, but also other compounds such as remaining unreacted reactants, water, basic compounds, lights, monoepoxide(s), heavies, solvent(s) and/or other additives such as inhibitors. The divinylarene dioxide containing crude feed stream may also result from a reaction mixture treated by stripping, washing, extraction, or other processing methods.

As an illustration of one embodiment of the present invention, a typical composition of the divinylarene dioxide-containing crude feed stream useful in the process of the present invention includes for example, but not limited thereto, the following:
(1) lights from 0.1 weight percent (wt %) to 75 wt %;
(2) monoepoxide(s) from 1 wt % to 30 wt %;
(3) divinylarene dioxide from 10 wt % to 98 wt %; and
(4) heavies from 0.1 wt % to 5 wt %.

The divinylarene dioxide-containing feed stream useful in the present invention process may be a single phase or multiphase mixture, that is, the feed stream mixture can comprise a single homogeneous phase; or the feed stream mixture can comprise more than one liquid and/or solid phases.

The divinylarene dioxide product of the present invention can be recovered from a feed stream mixture in any suitable manner taking into account the reactive nature of the divinylarene dioxide compounds, especially the tendency of the epoxide ring to undergo hydration or alcoholysis in aqueous media, slowly under neutral conditions and more rapidly under acidic or basic conditions.

The recovery process of the present invention may be carried out in various ways including for example, as a batch process, as a semi-batch process, as a continuous process, or a combination thereof. The recovery process of the present invention may be carried out using suitable equipment including for example stripping vessels, extraction units, flashes, centrifuges, agitators; condensers; a wiped film evaporator, a thin film evaporator, a falling film evaporator, a reboiler, a distillation column, a batch distill, or a combination thereof, and either in series or in parallel.

In addition, the recovery process and apparatus of the present invention may include suitable auxiliary equipment such one or more combinations of devices, instruments and equipment for processing the one or more effluents or streams of the process of the present invention, including for example vessels of any kind including for example filtration devices, tubes; pipes; heat exchangers; storage tanks; pumps; compressors; valves; flanges; any internal element used within any of the above devices such as column packing; and any other suitable equipment or connectors for processing the products of the present invention and/or for the consumption of such products in another process.

In one embodiment, one suitable method of recovering the divinylarene dioxide product may be by a separation process employing a suitable separator apparatus. The separation process may be used to obtain a divinylarene dioxide product purity such as divinylbenzene dioxide product purity of greater than (>) 85% in one embodiment; >90% in another embodiment; and >95% in yet another embodiment. In general, the divinylarene dioxide product purity such as divinylbenzene dioxide product purity may be from 85% to 99.999% in one embodiment; from 90% to 99.999% in another embodiment; from 95% to 99.999% in still another embodiment; from 97% to 99.999% in even yet another embodiment; and from 98% to 99.999% in even still another embodiment.

The separation process may obtain a divinylarene dioxide product recovery such as a divinylbenzene dioxide product recovery of >85% in one embodiment; >90% in another embodiment; and >95% in yet another embodiment. In one illustrative embodiment, the general range of the divinylarene dioxide product recovery such as divinylbenzene dioxide product recovery can be from 85% to 99%.

Generally, it is advantageous to recover a divinylarene dioxide product wherein the combination of percent recovery and percent purity of the divinylarene dioxide product recovered comprises a percent recovery of >85% and a percent purity of >85%, in one embodiment; a percent recovery of >85% and a percent purity of >90% in another embodiment; a percent recovery of >85% and a percent purity of >95% in yet another embodiment, a percent recovery of >90% and a percent purity of >about 90% in yet another embodiment, and a percent recovery of >95% and a percent purity of >95% in still another embodiment.

Generally, it is also advantageous to recover a divinylarene dioxide product wherein the percent of monoepoxides present in the product comprises less than (<) 15 wt % in one embodiment; <10 wt % in another embodiment; and <5 wt % in another embodiment; and <2 wt % in yet another embodiment.

In one embodiment, it is advantageous to recover a product comprising a divinylarene monoxide, an alkyl-vinyl-arene monoxide, or mixtures thereof; wherein the combination of percent recovery and percent purity of the product recovered comprises a percent recovery of >85% and a percent purity of >85%, in one embodiment; a percent recovery of >90% and a percent purity of >90% in another embodiment; and a percent recovery of >95% and a percent purity of >95% in still another embodiment In general, one embodiment of the separator apparatus used in the present invention may be an evaporator or a reboiler. Advantageously, the wall temperature of the evaporator or reboiler is controlled at <200° C. in one embodiment; at <180° C. in another embodiment; at <160° C. in still another embodiment; and at <140° C. in yet another embodiment. In one illustrative embodiment, the wall temperature of the evaporator or reboiler may be controlled at a general temperature range of from 100° C. to 200° C. If the wall temperature is above the aforementioned ranges, fouling may occur in the evaporator or reboiler, and the risk of runaway reaction may increase.

The evaporator or reboiler liquid phase turbulence as defined by Reynolds number is generally >2,000 in one embodiment; >25,000 in another embodiment; >100,000 in still another embodiment; and >200,000 in yet another embodiment. In one illustrative embodiment, the evaporator or reboiler liquid phase turbulence as defined by Reynolds number may be from 2,000 to 380,000. If the turbulence is below the aforementioned ranges, fouling may occur in the evaporator or reboiler.

The evaporator or reboiler liquid phase flux at the wall is generally >240 lb/sq-ft/hr in one embodiment; >500 lb/sq-ft./hr in another embodiment; >1,000 lb/sq-ft/hr in still another embodiment; and >2,000 lb/sq-ft/hr in yet another embodiment. In one illustrative embodiment, the evaporator or reboiler liquid phase flux at the wall can be from 240 lb/sq-ft./hr to 5,000,000 lb/sq-ft./hr; from 500 lb/sq-ft./hr to 3,000,000 lb/sq-ft./hr in another illustrative embodiment; from 1,000 lb/sq-ft/hr to 1,000,000 lb/sq-ft./hr in still another illustrative embodiment; and from 2,000 lb/sq-ft/hr to 100,000 lb/sq-ft./hr in yet another illustrative embodiment. If the liquid phase flux is below or above the aforementioned ranges, fouling may occur in the evaporator or reboiler.

The heavies content in the evaporator or reboiler is generally <60 wt % in one embodiment; <40 wt % in another embodiment; <30 wt % in still another embodiment; and <20 wt % in yet another embodiment. In one illustrative embodiment, the heavies content in the evaporator reboiler can be from 22 wt % to 31 wt %.

The distillation is operated at a reflux ratio of generally between 0.01 and 20 in one embodiment; between 0.05 and 10 in another embodiment; and between 0.1 and 5 in still another embodiment.

Depending on the relative boiling points of the divinylarene dioxide as compared to that of any co-products present in the feed mixture, the co-products can be recovered before or after distilling off the divinylarene dioxide. For example, flash distillation under approximately neutral conditions, using reduced pressure, may be a preferred method for recovering the epoxide with reduced levels of other co-products.

In another embodiment, extraction followed by distillation may be another method that can be used to recover the divinylarene dioxide. The extraction process useful in the present invention process can be any suitable extraction process such as an extraction process described in U.S. Patent Application Ser. No. 61/424,322.

Any suitable means can be used to distill the crude divinylarene dioxide product including for example flash distillation. For example, the distillation may be carried out generally at a temperature of from 60° C. to 200° C. in one embodiment; from 90° C. to 200° C. in another embodiment; from 100° C. to 195° C. in yet another embodiment; and from 130° C. to 170° C. in still another embodiment. At temperatures above the aforementioned ranges, the risk of runaway reaction may increase.

The pressure of the distillation may be generally from 0.1 mmHg to 700 mmHg in one embodiment; from 0.1 mmHg to 100 mmHg in another embodiment; from 0.1 mmHg to 25 mmHg in yet another embodiment; and from 0.1 mmHg to 20 mmHg in still another embodiment.

The residence time of the distillation may be generally from 1 second to 2 hours in one embodiment; from 5 seconds to 1 hours in another embodiment; from 10 seconds to 30 minutes in yet another embodiment; and from 30 seconds to 5 minutes in still another embodiment. At residence times longer than the aforementioned ranges, the risk of runaway reaction may increase.

The evaporator or reboiler liquid residence time is generally <5 minutes in one embodiment; <2 minutes in another embodiment; <1 minute in still another embodiment; <30 seconds in yet another embodiment; and <15 seconds in even yet another embodiment. In one illustrative embodiment, the general range of the evaporator or reboiler liquid residence time can be from 1 second to 120 seconds. At residence times longer than the aforementioned ranges, the risk of runaway reaction may increase.

Thermal treatment of the divinylarene dioxide product of the present invention during the recovery step (distillation and/or purification) for an extended time can result in oligomer formation including for example oligomers such as dimers, trimers, and/or tetramers of the epoxide produced in the reaction step, and/or result in runaway reaction caused by an autocatalyzed, self-heating, exothermic, ring-opening reaction of the epoxide. To minimize oligomer formation and minimize the risk of runaway reaction, the purification may be done under vacuum conditions to minimize temperature and at low residence times.

The oligomers formed from the divinylarene dioxide product with sustained heating during distillation, may create a situation where the oligomer containing divinylarene dioxide becomes too viscous to flow out of the processing apparatus, and may also result in loss of recovery of the divinylarene dioxide product. Accordingly, in one optional embodiment, a "high boiling point pot boiler" compound may be added to the feed stream passing to the purification process at a quantity sufficient to maintain a process stream's flowability in the equipment used in the present invention. For example, to maintain the flowability property of a process stream, a high boiling point pot boiler compound can be added to the feed stream, or may be added to any intermediate stream upstream of a separation step, to achieve a final concentration in the residue of generally from 0.5 wt % to 80 wt % in one embodiment, from 1 wt % to about 40 wt % in another embodiment, from 5 wt % to 35 wt % in yet another embodiment, and from about 10 wt % to about 30 wt % in still another embodiment. The high boiling point pot boiler useful in the present invention generally has a boiling point higher than 280° C. at 1 atm (101325 Pa) and a vapor pressure of <20 Pa at 25° C.

Examples of the pot boiler suitable for use in the present invention include for example, mineral oils; liquid epoxy resins such as DER™ 383 and DER™ 331 (trademarks of The Dow Chemical Company); heat transfer fluids such as Thermia-C™ (trademark of Shell Company), Dowtherm MX™ (trademark of The Dow Chemical Company) and Dowtherm T™ (trademark of The Dow Chemical Company); or mixtures thereof. Optionally, the aforementioned embodiments of inhibitors and combinations thereof may be added to the feed stream during the distillation step or the purification step or to the apparatuses used in the recovery process to prevent the polymerization of residual ethylenic double bonds in the divinylarene dioxide product.

The other compounds in the feed stream mixtures such as un-reacted raw materials and extraction solvent present in the reaction feed stream effluent, can also be recovered by distillation.

With reference to FIG. 1, there is shown one embodiment of the process of the present invention, generally indicated by numeral 100, including a separator 110 with a divinylarene dioxide-containing crude feed stream 111 being fed into the separator 110. The divinylarene dioxide-containing crude feed stream 111 may be sourced from another process and equipment such as an effluent stream from a reactor 101 (shown in dotted lines) of an epoxidation reaction process for producing a divinylarene dioxide. The lights from the separator 110 are removed from the separator via stream 112 for recovery or further processing; and the bottoms from the separator 110 are removed from the separator via stream 113 for recovery or further processing. A "separator" may include for example one or more separation vessels for separating and/or recovering the product from the other compounds in the process.

Figure 2:
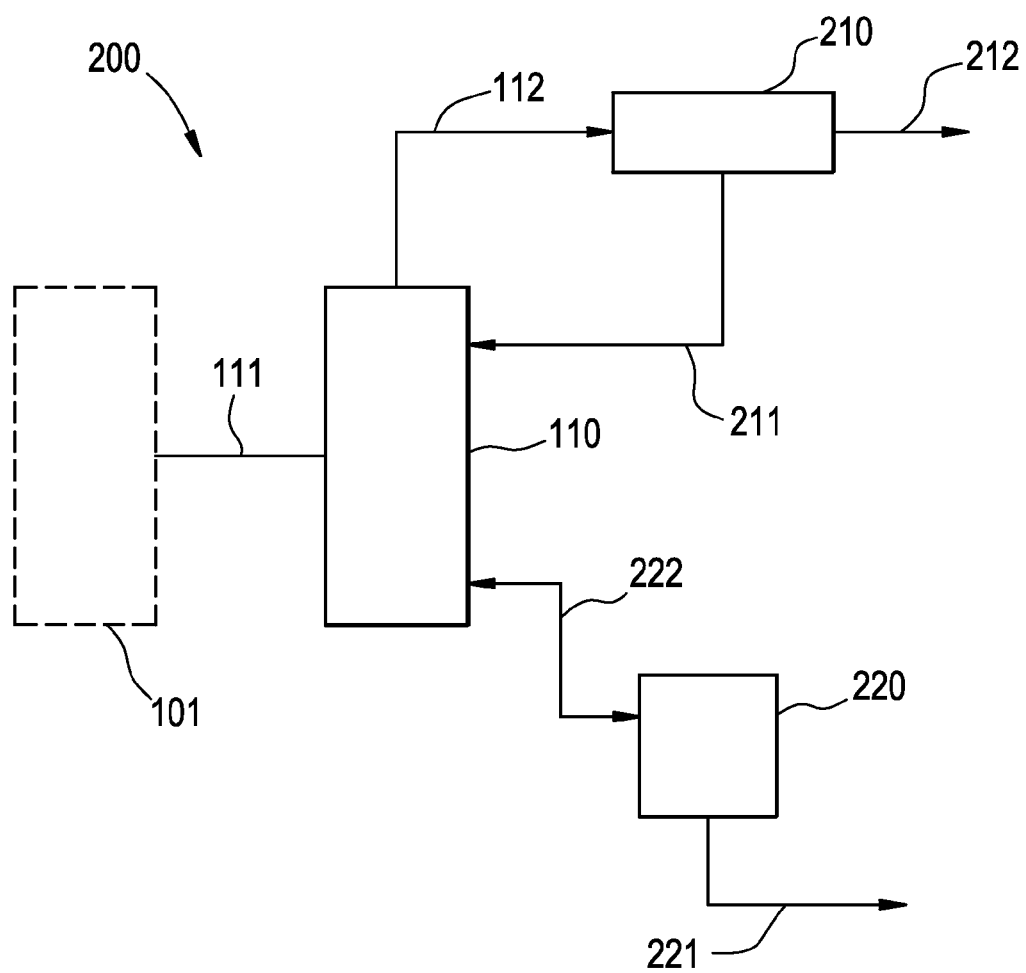

With reference to FIG. 2, there is shown another embodiment of the process of the present invention, generally indicated by numeral 200, including a separator such as distillation tower 110, a condenser 210 and a reboiler 220. A divinylarene dioxide-containing crude feed stream 111 is fed into the distillation tower 110. The divinylarene dioxide-containing crude feed stream 111 may be sourced from another process and equipment such as an effluent stream from a reactor 101 (shown in dotted lines) of an epoxidation reaction process for producing a divinylarene dioxide. The lights from the distillation tower 112 are removed from the tower via stream 112 and the bottoms of the tower are heated with the reboiler 220 via stream 222 and product is removed from the process 200 via stream 221 from the reboiler 220.

The lights from the distillation tower 110 are fed into a condenser 210 via stream 112 to condense the light components in stream 112. A portion of the condensed lights are recycled to the tower 110 via stream 211. The remaining lights leave the condenser 210 by stream 212. The stream 212 may contain for example a divinylarene monoxide, an alkyl-vinyl-arene monoxide, or mixtures thereof; and said stream 212 may be purified to form a purified lights product stream (not shown) for example of a divinylarene monoxide, an alkyl-vinyl-arene monoxide, or mixtures thereof. In addition, the purified lights stream after being purified may be sent to a further processing unit, recovered, purged, and/or recycled (not shown).

The feed stream 111 processed through the tower 110 may be for example, a reaction effluent from a reaction process for producing a divinylarene dioxide. The feed stream 111 may also result from a reaction mixture treated by stripping, washing, extraction, or other processing methods. The feed stream 111 may be the effluent of a mixture of compounds leaving the reactor 101 (shown in dotted lines) of such reaction process. Other ingredients in the feed stream 111 can include for example, unreacted compounds such as DVB, oxidant, catalyst, and other additives such as inhibitors, pot boilers, or partially reacted compounds such as monoepoxides. In another embodiment, solvent may be present in the feed stream 111, for example, if a preliminary extraction process utilizing an extraction solvent is used before the feed stream 111 is processed through the tower 110.

The feed stream 111 with all the components mixed therein is fed to the distillation apparatus 110 to carry out the separation/recovery of the desirable divinylarene dioxide product from the rest of the undesirable compounds in the feed stream 111. The desirable divinylarene dioxide product stream 221 from the reboiler 220 may be used "as is" or the product stream 221 may be introduced as a feed stream to a further separation/recovery apparatus, or other processing equipment (not shown).

The distillation apparatus 110 is adapted to separate the divinylarene dioxide product from the other reaction components in tower 110 sending the bottoms stream of the tower containing the product to the reboiler 220 via a stream 222. The product passes through the reboiler 220 and is recovered from the apparatus 220 via stream 221. The reaction components that are separated from the divinylarene dioxide product in apparatus 110 can also be sent to a further processing unit, recovered, purged, and/or recycled (not shown). Any of the recycle streams may require a periodic or continuous purge to limit the buildup of impurities. Any waste streams may also be removed from any of the apparatus of the present invention and sent to a waste recovery unit (not shown).

Figure 3:
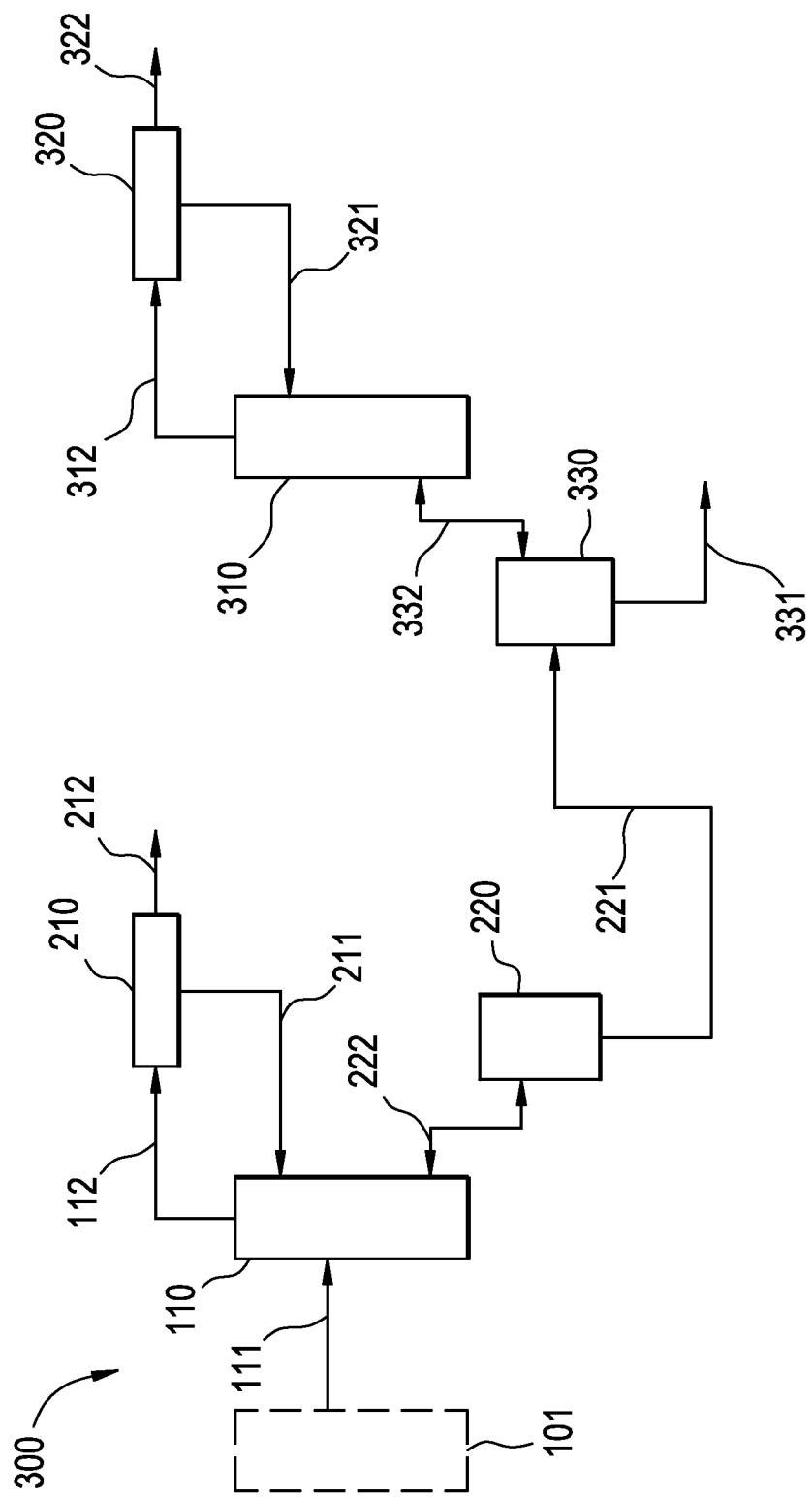

With reference to FIG. 3, there is shown another embodiment of the process of the present invention, generally indicated by numeral 300, including a distillation tower 110, a first condenser 210 and a first reboiler 220 as described with reference to FIG. 2. FIG. 3 also shows a divinylarene dioxide-containing crude feed stream 111 coming from a source such as an effluent stream from a reactor 101 (shown in dotted lines) of an epoxidation reaction process for producing a divinylarene dioxide. In addition, the process 300 includes a further purification process comprising purification apparatus 310, a second condenser 320 and a second reboiler 330. The product stream 221 from the first reboiler apparatus 220 may be introduced as a feed stream 221 to the purification apparatus 310 via the reboiler 330 wherein the product in feed stream 221 is further purified in the purification apparatus 310 and the second reboiler 330 to form a by-product stream containing heavies and low levels of divinylarene dioxide 331 leaving the apparatus 330. The divinylarene rich stream leaves the reboiler to the distillation tower 310 via stream 332.

A divinylarene dioxide rich stream 312 exiting from apparatus 310 is condensed in condenser 320. A portion of the condensed stream is recycled back to the apparatus 320 as stream 321. A divinylarene dioxide product stream exits the condenser 320 via stream 322. The divinylarene dioxide product stream 322 contains primarily divinylarene dioxide, and may contain small amounts of a divinylarene monoxide, an alkyl-vinyl-arene monoxide, heavies or mixtures thereof.

Figure 4:
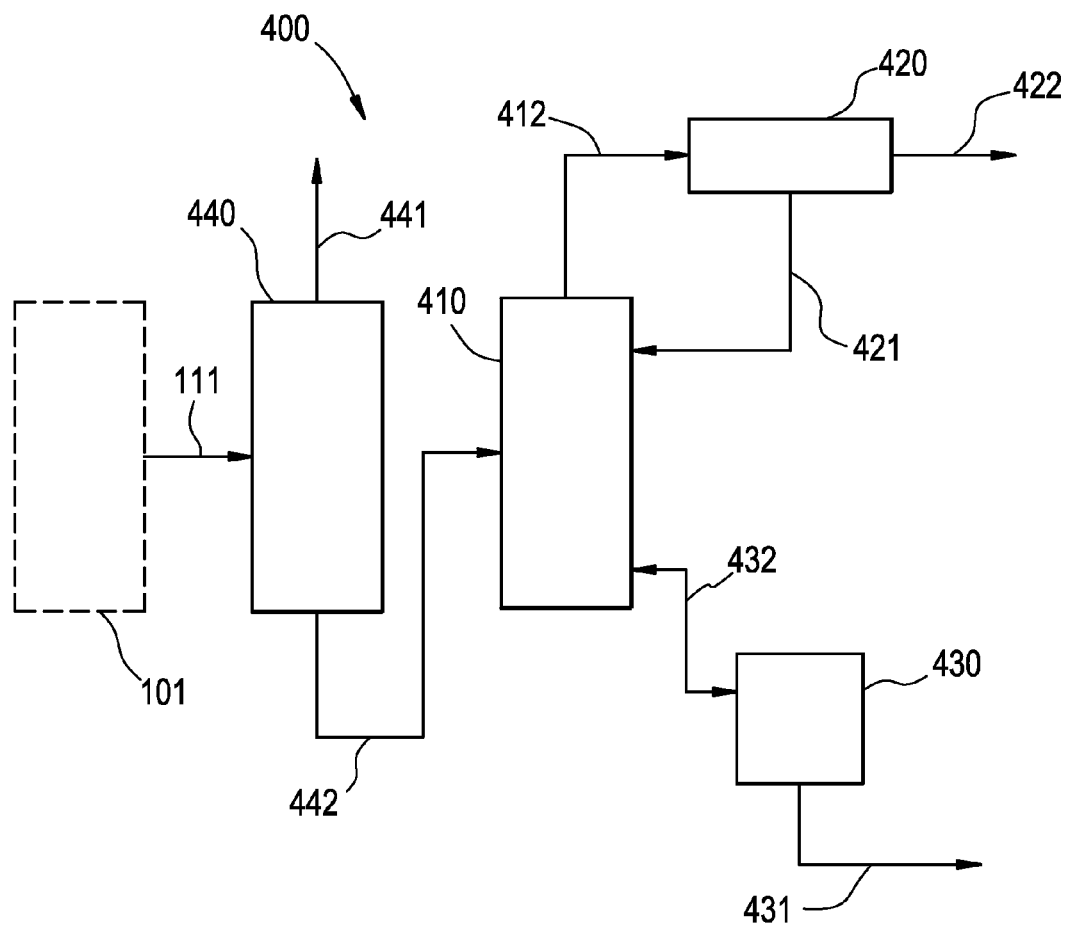

With reference to FIG. 4, there is shown another embodiment of the process of the present invention, generally indicated by numeral 400, including a distillation tower 410, a condenser 420 and a reboiler 430. In addition, the process 400 also includes a pretreatment apparatus 440, for pre-treating a crude feed stream 111 entering the pretreatment apparatus 440. The stream 111 is preferably pre-treated in a degassing apparatus 440 to remove the dissolved gases, water and lightest components from the stream 111 via stream 441 prior to being introduced into the distillation tower 410 as feed stream 442 exiting the apparatus 440. "Lightest components" herein means components such as water; solvents; methanol; acetonitrile; and dissolved gases such as $N_2$, $O_2$; with a boiling point of less than about 120° C. The dissolved gases, water and lightest components are removed via stream 441. FIG. 4 also shows the divinylarene dioxide-containing crude feed stream 111 coming from a source such as an effluent stream from a reactor 101 (shown in dotted lines) of an epoxidation reaction process for producing a divinylarene dioxide.

The divinylarene dioxide-containing crude feed stream 111 is fed into the apparatus 440, and the degassed stream 442 from the apparatus 440 is sent to the tower 410 as feed stream 442. Subsequently, similar to FIG. 2, a lights stream is removed from the distillation tower 410 via stream 412. The bottoms stream of the tower 410 are heated with the reboiler 430 via stream 432 and heavies are removed from the process 400 via stream 431 from the reboiler 430.

Figure 5:
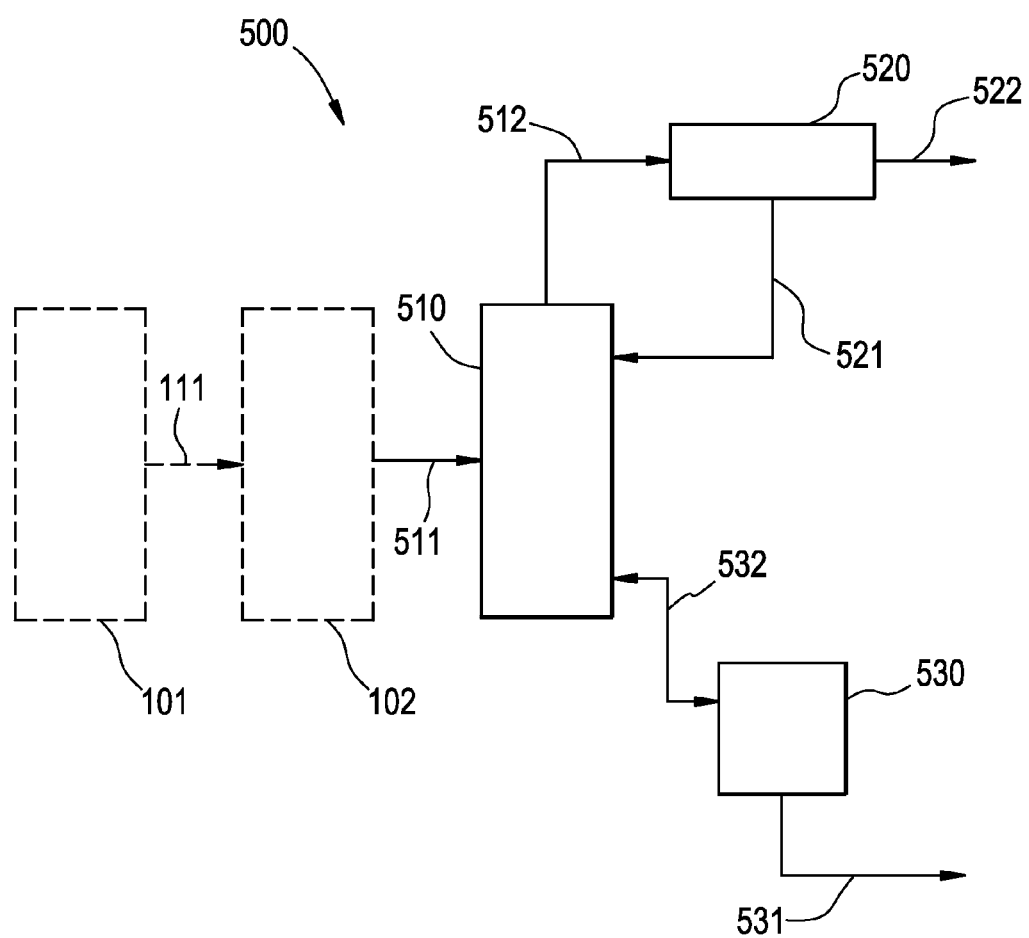

With reference to FIG. 5, there is shown still another embodiment of the process of the present invention, generally indicated by numeral 500, including a distillation tower 510, a condenser 520 and a reboiler 530. In the process 500 a crude feed stream 511 entering the apparatus 510 is a stream having been treated with an extraction solvent in apparatus 102 (shown in dotted lines) prior to being introduced into the distillation tower 510 as feed stream 511. FIG. 5 also shows a divinylarene dioxide-containing crude feed stream 111 originating from a source such as an effluent stream from a reactor 101 (shown in dotted lines) of an epoxidation reaction process for producing a divinylarene dioxide.

In FIG. 5 there is also shown the divinylarene dioxide-containing crude feed stream 111 being fed into the extraction apparatus 102 and the purified extraction stream 511 exiting the apparatus 102 which becomes the feed stream to the distillation tower 510. The feed stream 511 may contain a solvent concentration from less than 1% to 75% because of the pretreatment extraction process. Therefore, a solvent rich stream 511 is removed from the distillation tower 510 via stream 512. The bottoms stream of the tower 510 are heated with the reboiler 530 via stream 532 and product is removed from the process 500 via stream 531 from the reboiler 530.

The solvent from the distillation tower 510 is fed into a condenser 520 via stream 512 to condense the extraction solvent in stream 512. The condensed solvent is partially recycled to the tower via stream 521. Extraction solvent leaves the condenser 520 by stream 522. Stream 522 may be sent to a further processing unit, recovered, purged, and/or recycled (not shown).

In one embodiment, the product stream 531 from the apparatus 530 may be further processed by introducing the product stream 531 to a purification process/apparatus, such as the process/apparatus 200 shown in FIG. 2, or the process/apparatus 300 shown in FIG. 3; wherein the product stream 531 is further purified to form an even more purified product stream (not shown in FIG. 5). In addition, the purified stream after being purified may be sent to a further processing unit, recovered, purged, and/or recycled (not shown).

The above processes of the present invention may include one or more combinations of suitable devices, instruments and equipment for processing the one or more effluents or streams of the process of the present invention, including for example vessels of any kind; such as separators (batch, semi-batch or continuous), including for example stripping vessels, distillation columns, extraction units, filtration devices, flashes, evaporators, centrifuges, agitators; condensers; reboilers; tubes; pipes; heat exchangers; storage tanks; pumps; compressors; valves; flanges; any internal element used within any of the above devices such as column packing; and any other suitable equipment or connectors for processing the products of the present invention and/or for the consumption of such products in another process.

The divinylarene dioxide product recovered by the process of the present invention, particularly those derived from divinylbenzene such as for example divinylbenzene dioxide (DVBDO), are class of diepoxides which have a relatively low liquid viscosity but a higher rigidity than conventional epoxy resins.

The divinylarene dioxide recovered by the process of the present invention may comprise, for example, any substituted or unsubstituted arene nucleus bearing two vinyl groups in any ring position. The arene portion of the divinylarene dioxide may consist of benzene, substituted benzenes, or (substituted) ring-annulated benzenes or homologously bonded (substituted) benzenes, or mixtures thereof. The divinylarene portion of the divinylarene dioxide may be ortho, meta, or para isomers or any mixture thereof. Additional substituents may consist of oxidant-resistant groups including saturated alkyl, aryl, halogen, nitro, isocyanate, or R'O— wherein R' may be the same as defined above. Ring-annulated benzenes may consist of naphthalene, tetrahydronaphthalene. Homologously bonded (substituted) benzenes may consist of biphenyl, and diphenylether.

The divinylarene dioxide product recovered by the process of the present invention may be illustrated generally by general chemical Structures I-IV as follows:

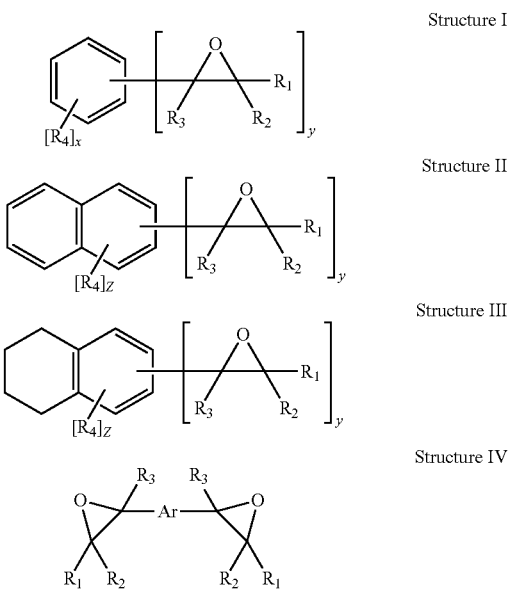

In the above Structures I-IV of the divinylarene dioxide product of the present invention, each $R_1$, $R_2$, $R_3$ and $R_4$ individually may be hydrogen, an alkyl, cycloalkyl, an aryl or an aralkyl group, where the alkyl, cycloalkyl, aryl, and aralkyl groups may have from 1 to about 18 carbon atoms, preferably from 1 to 4 carbon atoms; or a oxidant-resistant group including for example a halogen, a nitro, an isocyanate, or an WO group, wherein R' may be an alkyl, aryl or aralkyl group having from 1 to about 18 carbon atoms, preferably from 1 to 4 carbon atoms; x may be an integer of 0 to 4; y may be an integer greater than or equal to 2; x+y may be an integer less than or equal to 6; z may be an integer of 0 to 6; z+y may be an integer less than or equal to 8; and Ar is an arene fragment including for example, 1,3-phenylene group.

The divinylarene dioxide product recovered by the process of the present invention may include for example alkyl-vinyl-arene monoxides depending on the presence of alkyl-vinyl-arene in the starting material. The structure of the divinylarene dioxide, and composition of structural isomers, is determined by the divinylarene feedstock used. The reaction to epoxidize the ethylenic bonds do not generally impact the isomer distribution of the reactants as they are converted.

In one embodiment of the present invention, the divinylarene dioxide recovered by the process of the present invention may include for example divinylbenzene dioxide, divinylnaphthalene dioxide, divinylbiphenyl dioxide, divinyldiphenylether dioxide, and mixtures thereof.

In a preferred embodiment of the present invention, the divinylarene dioxide recovered by the process of the present invention may be for example DVBDO. Most preferably, the divinylarene dioxide component of the present invention includes, for example, a DVBDO as illustrated by the following chemical formula of Structure V:

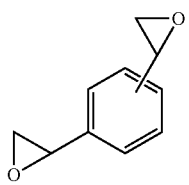

Structure V

The chemical formula of the above DVBDO compound may be as follows: $C_{10}H_{10}O_2$; the molecular weight of the DVBDO is about 162.2; and the elemental analysis of the DVBDO is about: C, 74.06; H, 6.21; and O, 19.73 with an epoxide equivalent weight of about 81 g/mol.

Divinylarene dioxides, particularly those derived from divinylbenzene such as for example DVBDO, are class of diepoxides which have a relatively low liquid viscosity but a higher rigidity and crosslink density than conventional epoxy resins.

Structure VI below illustrates an embodiment of a preferred chemical structure of the DVBDO useful in the present invention:

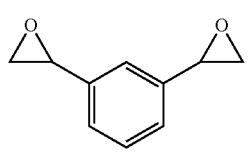

Structure VI

Structure VII below illustrates another embodiment of a preferred chemical structure of the DVBDO useful in the present invention:

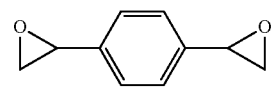

Structure VII

When DVBDO is prepared by known epoxidation processes, it may be possible to obtain one of three possible isomers: ortho, meta, and para. Accordingly, the present invention includes a DVBDO illustrated by any one of the above structures individually or as a mixture thereof. Structures VI and VII above show the meta (1,3-DVBDO) isomer of DVBDO and the para (1,4-DVBDO) isomer of DVBDO, respectively. The ortho isomer is rare; and usually DVBDO is mostly produced generally in a range of from 9:1 to 1:9 ratio of meta isomer (Structure VI) to para isomer (Structure VII). The present invention preferably includes as one embodiment a range of from 6:1 to 1:6 ratio of Structure VI to Structure VII, and in other embodiments the ratio of Structure VI to Structure VII may be from 4:1 to 1:4 or from 2:1 to 1:2.

The feedstock may also contain impurities including, but not limited to, ethylvinylbenzene (EVB), naphthalene, polyethylbenzenes (e.g. diethylbenzene, triethylbenzene, tetraethylbenzene, pentaethylbenzene, diphenylethane, other aklylated benzenes, and higher molecular weight oils), free radical inhibitors, or mixtures thereof. The divinylbenzene content of the feed may be greater than 55% in one embodiment; greater than 63% in another embodiment; greater than 80% in still another embodiment; greater than 90% in still another embodiment; or greater than 95% in yet another embodiment. The amount of co-product EVBO that is produced and that must be separated to obtain higher purity DVBDO is determined by DVB feed stock composition. In one preferred embodiment, the divinylarene feed stock purity may be greater than about 80%.

In one embodiment, the recovered divinylarene dioxide is a low viscosity liquid epoxy resin. The viscosity of the divinylarene dioxide recovered by the process of the present invention ranges generally from about 10 mP-s to about 100 mP-s; preferably, from 10 mP-s to 50 mP-s; and more preferably, from 10 mP-s to 25 mP-s at 25° C.

The utility of the divinylarene dioxides of the present invention may be advantageously their thermal stability to allow their formulation or processing at moderate temperatures (for example, at from 100° C. to 200° C.) for up to several hours (for example, for at least 2 hours) without oligomerization or homopolymerization. Oligomerization or homopolymerization during formulation or processing may be evident by a substantial increase in viscosity or gelling (crosslinking). The divinylarene dioxides of the present invention have sufficient thermal stability such that they do not experience a substantial increase in viscosity or gelling during formulation or processing at moderate temperatures.

The color of the divinylarene dioxide product when recovered as an intermediate stream from the bottoms of a separation step by the process of the present invention may be generally less than 2,500 APHA in one embodiment, less than 750 APHA in another embodiment, and less than 300 APHA in even yet another embodiment.

The color of the divinylarene dioxide product as the product is first produced as a distillate or overheads of a separation step by the process of the present invention may be less than 200 APHA in one embodiment, less than 100 APHA in still another embodiment, less than 60 APHA in yet another embodiment, and less than 50 APHA in even yet another embodiment, as APHA color is measured by the test described in ASTM D1209.

The color of the divinylarene dioxide product when recovered as a distillate or overheads recovered from a residue stream in a single evaporation stage by the process of the present invention may be generally less than 2,000 APHA in one embodiment, and less than 1,300 APHA in another embodiment.

The high purity divinylarene dioxide products of the present invention may be useful in various end uses including for example, for the preparation of epoxy resin compositions or formulations which, in turn, may be useful for preparing thermosets or cured products in the form of coatings, films, adhesives, laminates, composites, and electronics. The high purity divinylarene dioxide product of the present invention may be used alone or in a formulation to form a curable composition to manufacture various composites.

As a general illustration of the present invention, resin compositions based on the divinylarene dioxide products of the present invention may be useful for casting, potting, encapsulation, molding, and tooling. For example, the present invention may be used in electrical casting, applications; for plastic molding and tooling; and for the fabrication of composites parts. In addition, an assortment of optional additives may be added to the resin composition of the present invention in concentrations including for example, other resins, stabilizers, fillers, plasticizers, catalyst de-activators; and mixtures thereof.

EXAMPLES

The following examples and comparative examples further illustrate the present invention in detail but are not to be construed to limit the scope thereof.

In the following Examples, various terms and designations are used such as for example: "Percent purity (% purity)" herein means the mass concentration of a species in a process stream as measured by GC, and expressed as a percentage; and "Percent recovery (% recovery)" herein means the mass of a species obtained as a product divided by the mass of the species in the feed to the process expressed as a percentage.

In the following Examples, standard analytical equipment and methods are used such as for example, gas chromatography (GC) to determine the concentration of products, byproducts and impurities in the various process streams, and gel permeation chromatography (GPC) to determine the concentration of heavies in the various process streams.

Example 1

Recovery of DVBDO Using a Mini-Plant Process

Pass 1: A crude feed stream of DVBDO was fed to a distillation apparatus similar to one illustrated in FIG. 2. The crude feed stream comprised 74.1% DVBDO, 20.2% monoepoxides, 1.7% lights and 4.0% heavies (by weight). The distillation tower was nominal 0.1 meter (m) inside diameter with 0.91 m of packed height. The wiped film evaporator reboiler included 0.11 square meter ($m^2$) of heat transfer surface area. The mixture was distilled at a continuous feed rate of 2.7 kilograms per hour (kg/hr). The distillation was carried out at a nominal 0.23 kPa overhead pressure with a bottoms temperature of nominally 140° C. Reflux to the tower (stream 211) was controlled at a nominal 2 kg/hr and 13° C. from the condenser (210). The reboiler was operated at a liquid phase Reynolds number of about 89,000 and a process wall or skin temperature of less than about 190° C. Liquid phase residence time in the reboiler was less than about 25 seconds (s). A lights product (stream 212) was produced at 87.9% monoepoxide purity with 9.1% DVBDO (by weight). The balance of impurities was comprised of light and heavy components from the crude feed stream. Monoepoxide recovery to the lights product was 95.7%. The bottoms product (stream 221) was produced at 93.2% DVBDO purity and 1.5% lights (by weight). DVBDO recovery was 97.3%. Heavies increased by 1.2% (total heavies in products/heavies in feed*100%).

Pass 2: The bottoms product from Pass 1 above was collected, stored and subsequently fed into the same distillation apparatus as in Pass 1 above. The mixture was distilled at a continuous feed rate of 1.7 kg/hr. The distillation was carried out at a nominal 0.02 kPa overhead pressure with a reboiler temperature of nominally 130° C. Reflux to the tower (stream 211) was controlled at a nominal 1.5 kg/hr and 25° C. from the condenser (210). The reboiler was operated at a liquid phase Reynolds number of about 89,000 and a process wall or skin temperature of less than about 175° C. Liquid phase residence time in the reboiler was less than about 25 s. An overhead DVBDO rich product (stream 212) was produced at 97.8% DVBDO purity (by weight). DVBDO recovery to the overhead product was 88.9%. The bottoms product (stream 221) was produced at 32.5% heavies (by weight). Heavies did not increase across the distillation (total heavies in products was less than or equal to ($\leq$) heavies in feed).

Overall DVBDO recovery for the combined two passes above was calculated as (97.3%*88.9%)=86.5%.

Example 2

Recovery of DVBDO Using a Pilot Plant Process

Pass 1: A crude feed stream of DVBDO was fed to a distillation apparatus similar to one illustrated in FIG. 4. The crude feed stream comprised 73.1% DVBDO, 18.5% monoepoxides, 2.2% lights, 5.1% heavies and 1.1% water (by weight). The distillation tower was nominal 0.3 m inside diameter with 2.74 m of packed height. The wiped film evaporator reboiler included 0.4 $m^2$ of heat transfer surface area. The mixture was distilled at a continuous feed rate of 28 kg/hr. The distillation was carried out at a nominal 0.13 kPa overhead pressure. Reflux ratio to the tower (stream 421 rate divided by stream 422 rate) was controlled at a nominal 2:1 and 30° C. from the condenser (420). The reboiler was operated at a liquid phase Reynolds number of about 380,000 and a process wall or skin temperature of less than about 170° C. Liquid phase residence time in the reboiler was less than about 20 seconds. A lights product (stream 422) was produced at 96.2% monoepoxide purity with 0.7% DVBDO (by weight). The balance of impurities was comprised of light and heavy components from the crude feed stream. Monoepoxide recovery to the Lights Product was 94.5%. The Bottoms Product (stream 431) was produced at 92.3% DVBDO purity and 1.8% lights (by weight). DVBDO recovery was 99.6%. Heavies did not increase across the distillation (total heavies in products≤heavies in feed).

Pass 2: The bottoms product from Pass 1 above was collected, stored and subsequently fed into a distillation apparatus similar to one illustrated in FIG. 2. The mixture was distilled at a continuous feed rate of 11 kg/hr. The distillation was carried out at a nominal 0.23 kPa overhead pressure. Reflux ratio to the tower (stream 211 rate divided by stream 212 rate) was controlled at a nominal 1:10 and 30° C. from the condenser (210). The reboiler was operated at a liquid phase Reynolds number of about 380,000 and a process wall or skin temperature of less than about 170° C. Liquid phase residence time in the reboiler was less than about 20 seconds. An overhead DVBDO rich product (stream 212) was produced at 97.0% DVBDO purity (by weight). DVBDO recovery to the overhead product was 90.3%. The bottoms product (stream 221) was produced at 25.0% heavies (by weight). Heavies did not increase across the distillation (total heavies in products≤heavies in feed).

Pass 3: The bottoms residue from Pass 2 above was further processed in a short path distillation apparatus to recover additional DVBDO rich product. The short path evaporator heat transfer area was 0.2 m². The mixture was distilled at a continuous feed rate of 30 kg/hr. The distillation was carried out at a nominal 0.05 kPa overhead pressure with an evaporator temperature of nominally 120° C. and a condenser temperature of 30° C. The reboiler was operated at a liquid phase Reynolds number of about 34,000 and a process wall or skin temperature of less than about 120° C. Liquid phase residence time in the reboiler was less than about 25 seconds. An overhead DVBDO rich product was produced at 91.9% DVBDO purity (by weight). DVBDO recovery to the overhead product was 91.5%. The bottoms product was produced at 44.8% heavies (by weight). Heavies did not increase across the distillation (total heavies in products≤heavies in feed).

The cumulative DVBDO recovery for the above three passes was calculated as follows: (99.6%)*{(90.3%)+[(91.5%)*(100%-90.3%)]}=98.8%.

Example 3

Recovery of Solvent from Feed Stream Using a Mini-Plant Process

A solvent-rich crude feed stream of DVBDO was fed to a distillation apparatus similar to one illustrated in FIG. 5. The crude feed stream comprised 56.6% toluene, 37.8% DVBDO, 2.2% monoepoxides, 2.2% lights and 1.2% heavies (by weight). The distillation tower was nominal 0.1 m inside diameter with 0.91 m of packed height. The wiped film evaporator reboiler included 0.11 m² of heat transfer surface area. The mixture was distilled at a continuous feed rate of 3.0 kg/hr. The distillation was carried out at a nominal 3.3 kPa overhead pressure with a bottoms temperature of nominally 145° C. The condenser (520) was controlled at a nominal 0° C. with no reflux. The reboiler was operated at a liquid phase Reynolds number of about 89,000 and a process wall or skin temperature of less than about 190° C. Liquid phase residence time in the reboiler was less than 25 seconds. A solvent rich product (stream 522) was produced at 98.9% toluene purity with 0.4% DVBDO (by weight). Toluene recovery was 79.8%. The balance of impurities was comprised of light and heavy components from the crude feed stream. The bottoms product (stream 531) was produced at 0.6% toluene concentration (by weight). DVBDO purity was 87.5%. DVBDO recovery was 99.5%.

Example 4

Recovery of DVBDO Using a Multi-Stage Evaporator Pilot Plant Process

Pass 1: A degassed crude feed stream of DVBDO was fed to a short path distillation apparatus. The crude feed stream comprised 72.6% DVBDO, 22.5% lights, water and monoepoxides and 4.85% heavies (by weight). The short path evaporator heat transfer area was 0.2 m². The mixture was distilled at a continuous feed rate of 14.5 kg/hr. The distillation was carried out at a nominal 0.065 kPa overhead pressure. The evaporator was operated at a liquid phase Reynolds number of about 170,000 and a process wall or skin temperature of less than about 80° C. Liquid phase residence time in the reboiler was less than about 7 seconds. An overhead product was produced at 44% lights content with 56% DVBDO (by weight). The Bottoms Product was produced at 88.4% DVBDO purity and 2.4% lights (by weight). DVBDO recovery was 67%. Heavies did not increase across the distillation (total heavies in products≤heavies in feed).

Pass 2: The overhead product from Pass 1 above was collected, stored and subsequently fed into a short path distillation apparatus. The short path evaporator heat transfer area was 0.2 m². The mixture was distilled at a continuous feed rate of 15.5 kg/hr.

The distillation was carried out at a nominal 0.2 kPa overhead pressure. The evaporator was operated at a liquid phase Reynolds number of about 170,000 and a process wall or skin temperature of less than about 80° C. Liquid phase residence time in the reboiler was less than about 6 seconds. An overhead product was produced at 80.9% lights purity with 19.1% DVBDO (by weight). The Bottoms Product was produced at 73% DVBDO purity and 25.8% lights (by weight). DVBDO recovery was 91.3%. Heavies did not increase across the distillation (total heavies in products≤heavies in feed).

Pass 3: The bottoms product from Pass 2 above was collected, stored and subsequently fed into a short path distillation apparatus. The short path evaporator heat transfer area was 0.2 m². The mixture was distilled at a continuous feed rate of 15.5 kg/hr. The distillation was carried out at a nominal 0.053 kPa overhead pressure. The evaporator was operated at a liquid phase Reynolds number of about 170,000 and a process wall or skin temperature of less than about 80° C. Liquid phase residence time in the reboiler was less than about 6 seconds. An overhead product was produced at 42.4% lights purity with 57.6% DVBDO (by weight). The Bottoms Product was produced at 96.7% DVBDO purity and 2.5% lights (by weight). DVBDO recovery was 66.2%. Heavies did not increase across the distillation (total heavies in products≤heavies in feed).

Pass 4: The bottoms products from Pass 1 and Pass 3 above were collected, stored and subsequently fed into a short path distillation apparatus. The short path evaporator heat transfer area was 0.2 m². The mixture was distilled at a continuous feed rate of 19.5 kg/hr. The distillation was carried out at a nominal 0.033 kPa overhead pressure. The evaporator was operated at a liquid phase Reynolds number of about 170,000 and a process wall or skin temperature of less than about 90° C. Liquid phase residence time in the reboiler was less than about 12 seconds. An overhead product was produced at 96.2% DVBDO purity with 0.7% heavies (by weight). The balance of impurities was comprised of light and heavy components from the crude feed stream. The Bottoms Product was produced at 72.6% DVBDO purity and 17.2% heavies (by weight). DVBDO recovery was 72.9%. Heavies did not increase across the distillation (total heavies in products≤heavies in feed).

Pass 5: The bottoms residue from Pass 4 above was further processed in a short path distillation apparatus. The short path evaporator heat transfer area was 0.2 m². The mixture was distilled at a continuous feed rate of 25 kg/hr. The distillation was carried out at a nominal 0.047 kPa overhead pressure. The evaporator was operated at a liquid phase Reynolds number of about 34,000 and a process wall or skin temperature of less than about 105° C. Liquid phase residence time in the reboiler was less than about 12 seconds. An overhead DVBDO rich product was produced at 95.1% DVBDO purity (by weight). DVBDO recovery to the overhead product was 87.7%. The bottoms product was produced at 45.4% heavies (by weight). Heavies did not increase across the distillation (total heavies in products≤heavies in feed).

Pass 6: The overheads product from Pass 5 above was collected, stored and subsequently fed into a short path distillation apparatus. The short path evaporator heat transfer area was 0.2 m². The mixture was distilled at a continuous feed rate of 19.5 kg/hr. The distillation was carried out at a nominal 0.033 kPa overhead pressure. The evaporator was operated at a liquid phase Reynolds number of about 170,000 and a process wall or skin temperature of less than about 90° C. Liquid phase residence time in the reboiler was less than about 12 seconds. An overhead product was produced at 97.2% DVBDO purity with 0.8% heavies (by weight). The balance of impurities was comprised of light and heavy components from the crude feed stream. The Bottoms Product was produced at 97.4% DVBDO purity and 6.4% heavies (by weight). DVBDO recovery was 79.8%. Heavies did not increase across the distillation (total heavies in products≤heavies in feed).

The cumulative DVBDO recovery for the above six passes was calculated as follows: {(67%)+(100−67%)*91.3%}*{(72.9%)+(100−72.9%)*87.7}=93.9%.

Comparative Example A

Recovery of DVBDO by Batch Distillation

Divinylbenzene (DVB) used in this Comparative Example A contained 80% DVB and 20% ethylvinylbenzene (EVB). Into a 1-L 5-neck round bottom flask was charged DVB (67.0 g, 0.4117 mole DVB, 0.1015 mole EVB), acetonitrile (98.7 g, 2.4044 mole) and methanol solvent (234.5 g). The reaction flask was equipped with a Thermoscientific #8272BN pH probe connected to a Fisher Scientific Accumet® AR15 pH meter.

With vigorous stirring of the mixture, the resulting solution was warmed to 50° C., whereupon simultaneous addition of 51% $H_2O_2$ (80.17 g, 1.2022 mole) and 1N NaOH solution was begun. The $H_2O_2$ was added over a period of two hr while maintaining the reaction temperature at 50° C. and adding NaOH solution at a rate sufficient to maintain the pH at 10.0-10.1. The mixture was digested an additional 4 hours (hr) at 50° C. and pH 10.0-10.1. A total of 94.2 g of 1N NaOH (0.090 mol) was added in a total reaction time of six hours. The mixture was diluted with 500 mL of water and extracted three times with 210 g of chloroform. The combined extracts were washed two times with water (240 g). DVB conversion was 100%, DVBDO yield was 88%, and DVBMO yield was 2% based on DVB charged.

Solvent, including the chloroform, was removed by batch distillation giving 76.8 g of crude product at 76.9% DVBDO and 21.0% monoepoxides based on GC area %. Batch distillation of the crude product at 128° C. overhead temperature and 3 mmHg (400 Pa) pressure gave 17.8 g of a first distillate with 67.7% EVBO, 3.7% DVBMO, and 25.5% DVBDO, based on GC area percent analysis. This represents 78.9% recovery of monoepoxides. Further distillation at 133° C. overheads and 3 mmHg (400 Pa) pressure gave 44.5 g of DVBDO with 97.7% purity by GC area percent. This represents 75.3% recovery (44.5 g/59.1 g) of DVBDO product.

Comparative Example B

Recovery of DVBDO by Continuous Distillation

The recovery of DVBDO used in this Comparative Example B by continuous distillation was completed on a lab distillation set up. A 1-inch (25 mm) diameter, 6-tray Oldershaw glass column was used for the DVBDO distillation. A 1 L round bottom flask equipped with magnetic stir was used as the reboiler.

Pass 1 lights removal: A crude feed stream of DVBDO was fed to the distillation apparatus. The crude feed stream comprised 75.4% DVBDO, 20.9% monoepoxides based on GC area percent analysis. The crude was fed at a rate of 140 g/hr. The distillation apparatus was controlled at 97° C. and 3 mmHg on the top and 155° C. and 10 mmHg at the reboiler. A 40% reflux ratio of the overhead total condenser was used. The overhead lights stream at a rate of 22.2 g/hr comprised 1.8% DVBDO and 91.7% monoepoxides based on GC area percent analysis. The bottom stream at a rate of 117.7 g/hr (approximately 5 hr residence time) comprised 94.9% DVBDO and 2.5% monoepoxides based on GC area percent analysis. This represented a 100% recovery of the DVBDO product and 69.8% recovery of the monoepoxides.

Pass 2 DVBDO recover: The bottom stream with lights removed by the above Pass 1 was mixed with a high boiling point pot boiler (D.E.R. 383 liquid epoxy resin in particular) and fed to the same distillation apparatus for DVBDO recovery. The feed stream comprised 78.3% DVBDO, 1.7% monoepoxides and 17.2% pot boiler based on GC area percent analysis. The feed rate was 38.1 g/hr. The distillation apparatus was controlled at 115° C. and 2 mmHg on the top and 157° C. and 7 mmHg at the reboiler. The overhead total condenser reflux ratio was controlled between 25% and 30%. The product rate from the column top at a rate of 24.1 g/hr comprised 95.7% DVBDO and 2.8% monoepoxides based on GC area percent analysis. The bottom residual stream at a rate of 14.0 g/hr (approximately 24 hr residence time) comprised 56.8% DVBDO and 0.2% monoepoxides based on GC area percent analysis. The represented a 77.3% recovery of the DVBDO product and 100% recovery of the monoepoxides.

Comparative Example C

Recovery of DVBDO by WFE

A series of experiments were conducted to purify crude DVBDO mixtures in a single pass through a 2-inch (51 mm) wiped film evaporator (WFE) apparatus. The apparatus was operated as a short path evaporator with a cold finger, resulting in the collection of multiple overhead streams collected in a single pass.

The crude DVBDO feed used for these experiments was approximately 67 wt % DVBDO, 17.5% monoepoxides, and 3% heavies. Typical operating conditions included operating pressure of less than about 5 mmHg, a feed rate of 2-3 g/min, and a jacket temperature at about 150° C. The cold finger was operated at about 90 to 110° C., and the condenser was operated at 0 to 30° C.

The best operating conditions found were at a feed rate of about 2 g/min, a pressure of 2 mmHg, a jacket temperature of 150° C., a cold finger temperature of 100° C., and a condenser temperature of 30° C. At these conditions the DVBDO product purity recovered was 93% and the DVBDO recovery was 79%. The monoepoxide purity was 59% and the monoepoxide recovery was 77%.

The following Table I summarizes the results of the examples.

TABLE I

| Example | Scheme | DVBDO Recovery | DVBDO Purity | Monoepoxide Recovery | Monoepoxide Purity |
|---------|--------|----------------|--------------|----------------------|--------------------|
| 1 | Continuous Distillation | 86.5% | 97.8% | 95.7% | 87.9% |
| 2 | Continuous Distillation | 98.8% | 97.0% | 93.6% | 96.2% |
| 3 | Continuous Solvent Recovery | 99.5% | 87.6% | Solvent Recovery: 79.8% | Solvent Purity: 98.8% |
| 4 | Multi-stage Evaporator | 93.9% | 96.2% | Not analyzed | Not analyzed |
| Comp A | Batch Distillation | 75.3% | 97.7% | 78.9% | 71.4% |
| Comp B | Continuous Distillation | 77.3% | 95.7% | 79.8% | 91.7% |
| Comp C | WEE Distillation | 79% | 93% | 77% | 59% |

The process of the present invention is not to be limited by the specific examples set forth above including the tables to which they refer. Rather, these examples and the tables they refer to are illustrative of the process of the present invention.

The invention claimed is:

1. A process for recovering a divinylarene dioxide from a crude feed stream comprising (i) lights from 0.1 wt % to 75 wt %; (ii) monoepoxide(s) from 1 wt % to 30 wt %; (iii) divinylarene dioxide from 10 wt % to 98 wt %; and (iv) heavies from 0.1 wt % to 5 wt %;

the process comprising the steps of:
(a) providing the continuous crude feed stream to a separator
(b) separating/recovering the divinylarene dioxide product from the other compounds of the crude feed stream;
wherein the separation step (b) is one distillation step or a combination of two or more distillation steps; or one evaporator step or a combination of two or more evaporation steps; and
wherein the wall temperature of the distillation step or evaporation step is controlled at a temperature of less than 200° C.; wherein the residence time is less than 5 minutes; wherein the liquid phase turbulence as defined by Reynolds number is greater than 2000; wherein the liquid phase flux is greater than 240 lb/sq-ft/hr; wherein the heavies is less than 60 weight percent; and wherein the distillation and evaporation is operated at a reflux ratio between 0.01 and 20; and
(c) recycling the other compounds recovered from the feed stream back into step (a);
wherein the percent recovery of the divinylarene dioxide product recovered comprises greater than about 85 percent; and wherein the percent purity of the divinylarene dioxide product recovered comprises greater than about 85 percent.

2. The process of claim 1, including further the step of (c) purifying the divinylarene dioxide product recovered from step (b) to obtain a divinylarene dioxide product with greater than 90 percent purity.

3. The process of claim 1, wherein the percent of monoepoxides present in the product comprises less than about 15 weight percent.

4. The process of claim 1, wherein the divinylarene dioxide is divinylbenzene dioxide.

5. The process of claim 1, including further the step of separating/recovering a product comprising a divinylarene monoxide, an alkyl-vinyl-arene monoxide, or a mixture thereof.

6. The process of claim 5, including further the step of purifying the divinylarene monoxide, alkyl-vinyl-arene monoxide, or mixture thereof product.

7. The process of claim 6, wherein the purifying step comprises a distillation process to provide a divinylarene monoxide, an alkyl-vinyl-arene monoxide or mixture thereof product; wherein the percent recovery of the product recovered comprises greater than about 85 percent; and wherein the percent purity of the product recovered comprises greater than about 85 percent.

8. The process of claim 1, wherein the feed stream includes a solvent; and including further the step of removing the solvent prior to or after step (b).

9. The process of claim 1, including (i) diluting the reaction effluent with water; (ii) extracting the diluted reaction effluent of step (i) with an extraction solvent;
(iii) water washing an organic extract of step (ii) to remove one or more of residual compounds;
(iv) distilling the water washed organic extract of step (iii) to remove the extraction solvent; and
(v) recovering divinylarene dioxide product.

10. The process of claim 9, wherein the recovered solvent is recycled as an extraction agent to step (ii).

11. A process for recovering a divinylarene monoxide, an alkyl-vinyl-arene monoxide, or mixtures thereof from a crude feed stream comprising the steps of: (a) providing a crude feed stream containing at least one divinylarene monoxide, an alkyl-vinyl-arene monoxide, or mixtures thereof product and other compounds; and (b) separating/recovering the divinylarene monoxide, an alkyl-vinyl-arene monoxide, or mixtures thereof product from the other compounds of the crude feed stream from step (a); wherein the percent recovery of the divinylarene monoxide, an alkyl-vinyl-arene monoxide, or mixtures thereof product recovered comprises greater than about 85 percent; and wherein the percent purity of the divinylarene monoxide, an alkyl-vinyl-arene monoxide, or mixtures thereof product recovered comprises greater than about 85 percent.

* * * * *